United States Patent
Cappello et al.

(10) Patent No.: US 11,743,447 B2
(45) Date of Patent: Aug. 29, 2023

(54) GAZE TRACKING APPARATUS AND SYSTEMS

(71) Applicant: Sony Interactive Entertainment Inc., Tokyo (JP)

(72) Inventors: Fabio Cappello, London (GB); Maria Chiara Monti, London (GB); Alexander Smith, London (GB)

(73) Assignee: sony Interactive Entertainment Inc., Tokyo (JP)

( * ) Notice: Subject to any disclaimer, the term of this patent is extended or adjusted under 35 U.S.C. 154(b) by 5 days.

(21) Appl. No.: 17/340,282

(22) Filed: Jun. 7, 2021

(65) Prior Publication Data
US 2021/0392318 A1 Dec. 16, 2021

(30) Foreign Application Priority Data
Jun. 11, 2020 (GB) ...................................... 2008870

(51) Int. Cl.
| | | |
|---|---|---|
| H04N 13/383 | (2018.01) | |
| H04N 13/344 | (2018.01) | |
| G02B 27/00 | (2006.01) | |
| G02B 27/01 | (2006.01) | |

(52) U.S. Cl.
CPC ....... *H04N 13/383* (2018.05); *G02B 27/0093* (2013.01); *G02B 27/0179* (2013.01); *H04N 13/344* (2018.05); *G02B 2027/0187* (2013.01)

(58) Field of Classification Search
CPC ............ G02B 27/0093; G02B 27/0179; H04N 13/383; H04N 13/344
See application file for complete search history.

(56) References Cited

U.S. PATENT DOCUMENTS

| | | | |
|---|---|---|---|
| 9,135,508 B2 * | 9/2015 | Vaught | G06V 40/197 |
| 10,264,176 B2 * | 4/2019 | Kim | G06T 7/13 |
| 2013/0114850 A1 * | 5/2013 | Publicover | A61B 3/0025 |
| | | | 382/103 |
| 2014/0098198 A1 | 4/2014 | Lee | |

(Continued)

FOREIGN PATENT DOCUMENTS

KR 102006281 B 8/2019

OTHER PUBLICATIONS

Search and Examination Report for corresponding GB Application No. GB2008870.4, 9 pages, dated Oct. 21, 2020.

(Continued)

*Primary Examiner* — Neil R Mikeska
(74) *Attorney, Agent, or Firm* — Matthew B. Dernier, Esq.

(57) ABSTRACT

A gaze tracking system comprising a first camera operable to capture images of a user within an environment, a second camera, having a smaller field of view than the first camera, operable to capture images of at least one of the user's eyes, an eye identification unit operable to identify a location of at least one of the user's eyes from images captured by the first camera, a camera control unit operable to modify the position and/or orientation of the second camera in dependence upon the detected location of the at least one of the user's eyes, so as to cause the second camera to be able to capture images of at least one of the user's eyes, and a gaze direction identification unit operable to identify a gaze direction of the user from images captured by the second camera.

12 Claims, 11 Drawing Sheets

(56) References Cited

U.S. PATENT DOCUMENTS

| | | | |
|---|---|---|---|
| 2015/0077543 A1* | 3/2015 | Kerr | H04N 5/33 348/135 |
| 2016/0170208 A1* | 6/2016 | Border | G02B 27/0149 359/471 |
| 2016/0180591 A1* | 6/2016 | Shiu | G06F 1/163 345/633 |
| 2016/0210503 A1 | 7/2016 | Yin | |
| 2016/0363995 A1* | 12/2016 | Rougeaux | G02B 27/0093 |
| 2018/0032812 A1* | 2/2018 | Sengelaub | G06T 7/74 |
| 2019/0118091 A1 | 4/2019 | Taylor | |
| 2019/0147607 A1* | 5/2019 | Stent | G06F 3/012 382/103 |
| 2019/0278090 A1* | 9/2019 | Yehezkel | G06F 3/017 |
| 2019/0278091 A1* | 9/2019 | Smits | G03B 35/18 |
| 2020/0026350 A1* | 1/2020 | Eash | G06F 3/011 |
| 2020/0174262 A1* | 6/2020 | Godar | G06F 3/013 |
| 2021/0088790 A1* | 3/2021 | Forster | G02B 27/017 |

OTHER PUBLICATIONS

H. R. Chennamma, et al., "A survey on eye gaze tracking techniques," Indian Journal of Computer Science and Engineering, vol. 4, No. 5, pp. 388-393, Oct. 5, 2013.

Brevin Tilmon, et al., "FoveaCam: A MEMS Mirror-Enabled Foveating Camera," IEEE International Conference on Computational Photography (ICCP), 11 pages, Oct. 20, 2020.

* cited by examiner

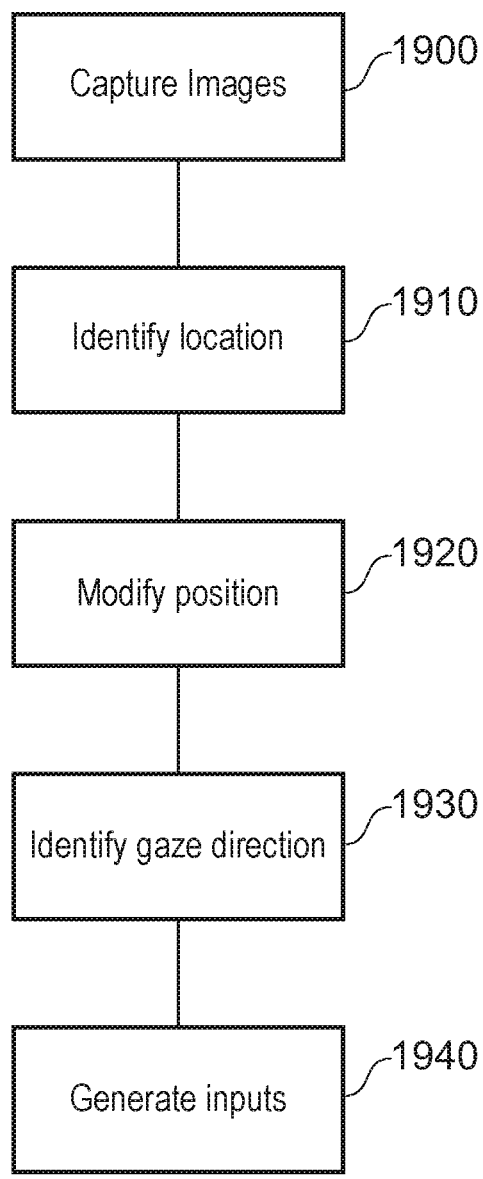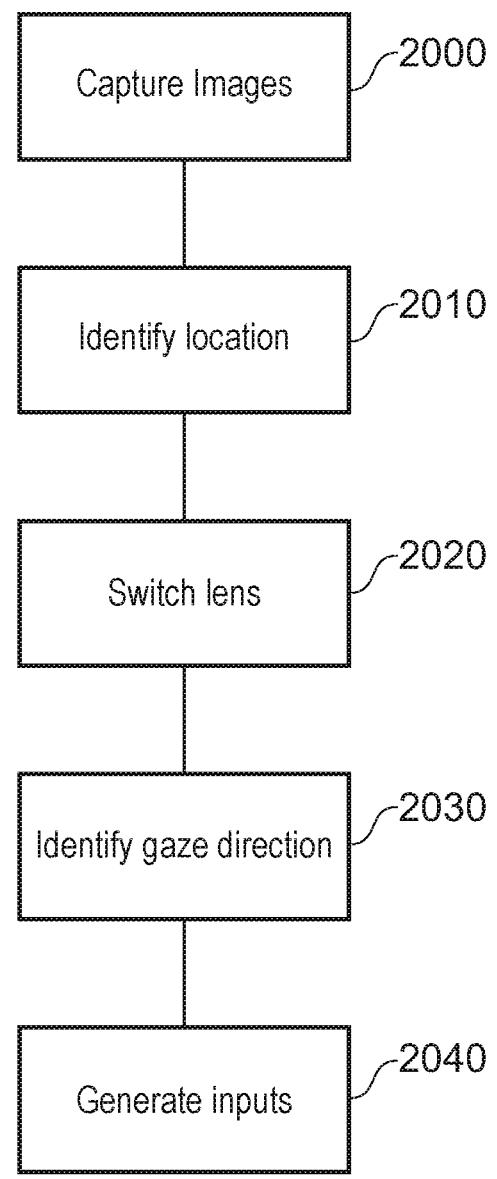
FIG. 19
FIG. 20

GAZE TRACKING APPARATUS AND SYSTEMS

BACKGROUND OF THE INVENTION

Field of the Invention

This disclosure relates to a gaze tracking system and method.

Description of the Prior Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

Gaze tracking systems are used to identify a location of a subject's gaze within an environment; in many cases, this location may be a position on a display screen that is being viewed by the subject. In a number of existing arrangements, this is performed using one or more inwards-facing cameras directed towards the subject's eye (or eyes) in order to determine a direction in which the eyes are oriented at any given time. Having identified the orientation of the eye, a gaze direction can be determined and a focal region may be determined as the intersection of the gaze direction of each eye.

One application for which gaze tracking is considered of particular use is that of use in head-mountable display units (HMDs). The use in HMDs may be of particular benefit owing to the close proximity of inward-facing cameras to the user's eyes, allowing the tracking to be performed much more accurately and precisely than in arrangements in which it is not possibly to provide the cameras with such proximity.

By utilising gaze detection techniques, it may be possible to provide a more efficient and/or effective processing method for generating content or interacting with devices.

For example, gaze tracking may be used to provide user inputs or to assist with such inputs—a continued gaze at a location may act as a selection, or a gaze towards a particular object accompanied by another input (such as a button press) may be considered as a suitable input. This may be more effective as an input method in some embodiments, particularly in those in which a controller is not provided or when a user has limited mobility.

Foveal rendering is an example of a use for the results of a gaze tracking process in order to improve the efficiency of a content generation process. Foveal rendering is rendering that is performed so as to exploit the fact that human vision is only able to identify high detail in a narrow region (the fovea), with the ability to discern detail tailing off sharply outside of this region.

In such methods, a portion of the display is identified as being an area of focus in accordance with the user's gaze direction. This portion of the display is supplied with high-quality image content, while the remaining areas of the display are provided with lower-quality (and therefore less resource intensive to generate) image content. This can lead to a more efficient use of available processing resources without a noticeable degradation of image quality for the user.

It is therefore considered advantageous to be able to improve gaze tracking methods, and/or apply the results of such methods in an improved manner. It is in the context of such advantages that the present disclosure arises.

SUMMARY OF THE INVENTION

This disclosure is defined by claim 1.

Further respective aspects and features of the disclosure are defined in the appended claims.

It is to be understood that both the foregoing general description of the invention and the following detailed description are exemplary, but are not restrictive, of the invention.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein:

FIG. 19 schematically illustrates a gaze tracking method using two cameras with different fields of view; and FIG. 20 schematically illustrates a gaze tracking method suitable for implementing embodiments in which a single camera is provided with multiple lenses.

DESCRIPTION OF THE EMBODIMENTS

Figure 1:
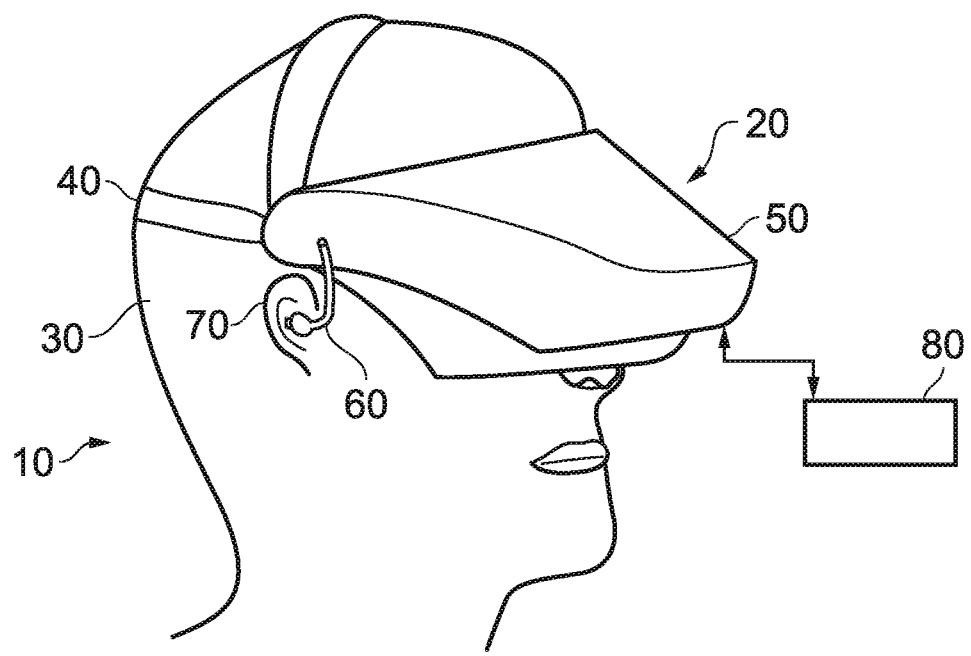
FIG. 1 schematically illustrates an HMD worn by a user.

Referring now to the drawings, wherein like reference numerals designate identical or corresponding parts throughout the several views, embodiments of the present disclosure are described. In FIG. 1, a user 10 is wearing an HMD 20 (as an example of a generic head-mountable apparatus—other examples including audio headphones or a head-mountable light source) on the user's head 30. The HMD comprises a frame 40, in this example formed of a rear strap and a top strap, and a display portion 50. As noted above, many gaze tracking arrangements may be considered particularly suitable for use in HMD systems; however, use with such an HMD system should not be considered essential.

Note that the HMD of FIG. 1 may comprise further features, to be described below in connection with other drawings, but which are not shown in FIG. 1 for clarity of this initial explanation.

The HMD of FIG. 1 completely (or at least substantially completely) obscures the user's view of the surrounding environment. All that the user can see is the pair of images displayed within the HMD, as supplied by an external processing device such as a games console in many embodiments. Of course, in some embodiments images may instead (or additionally) be generated by a processor or obtained from memory located at the HMD itself.

The HMD has associated headphone audio transducers or earpieces 60 which fit into the user's left and right ears 70. The earpieces 60 replay an audio signal provided from an external source, which may be the same as the video signal source which provides the video signal for display to the user's eyes.

The combination of the fact that the user can see only what is displayed by the HMD and, subject to the limitations of the noise blocking or active cancellation properties of the earpieces and associated electronics, can hear only what is provided via the earpieces, mean that this HMD may be considered as a so-called "full immersion" HMD. Note however that in some embodiments the HMD is not a full immersion HMD, and may provide at least some facility for the user to see and/or hear the user's surroundings. This could be by providing some degree of transparency or partial transparency in the display arrangements, and/or by projecting a view of the outside (captured using a camera, for example a camera mounted on the HMD) via the HMD's displays, and/or by allowing the transmission of ambient sound past the earpieces and/or by providing a microphone to generate an input sound signal (for transmission to the earpieces) dependent upon the ambient sound.

A front-facing camera 122 may capture images to the front of the HMD, in use. Such images may be used for head tracking purposes, in some embodiments, while it may also be suitable for capturing images for an augmented reality (AR) style experience. A Bluetooth® antenna 124 may provide communication facilities or may simply be arranged as a directional antenna to allow a detection of the direction of a nearby Bluetooth transmitter.

In operation, a video signal is provided for display by the HMD. This could be provided by an external video signal source 80 such as a video games machine or data processing apparatus (such as a personal computer), in which case the signals could be transmitted to the HMD by a wired or a wireless connection. Examples of suitable wireless connections include Bluetooth® connections. Audio signals for the earpieces 60 can be carried by the same connection. Similarly, any control signals passed from the HMD to the video (audio) signal source may be carried by the same connection. Furthermore, a power supply (including one or more batteries and/or being connectable to a mains power outlet) may be linked by a cable to the HMD. Note that the power supply and the video signal source 80 may be separate units or may be embodied as the same physical unit. There may be separate cables for power and video (and indeed for audio) signal supply, or these may be combined for carriage on a single cable (for example, using separate conductors, as in a USB cable, or in a similar way to a "power over Ethernet" arrangement in which data is carried as a balanced signal and power as direct current, over the same collection of physical wires). The video and/or audio signal may be carried by, for example, an optical fibre cable. In other embodiments, at least part of the functionality associated with generating image and/or audio signals for presentation to the user may be carried out by circuitry and/or processing forming part of the HMD itself. A power supply may be provided as part of the HMD itself.

Some embodiments of the invention are applicable to an HMD having at least one electrical and/or optical cable linking the HMD to another device, such as a power supply and/or a video (and/or audio) signal source. So, embodiments of the invention can include, for example:

(a) an HMD having its own power supply (as part of the HMD arrangement) but a cabled connection to a video and/or audio signal source;

(b) an HMD having a cabled connection to a power supply and to a video and/or audio signal source, embodied as a single physical cable or more than one physical cable;

(c) an HMD having its own video and/or audio signal source (as part of the HMD arrangement) and a cabled connection to a power supply; or (d) an HMD having a wireless connection to a video and/or audio signal source and a cabled connection to a power supply.

If one or more cables are used, the physical position at which the cable enters or joins the HMD is not particularly important from a technical point of view. Aesthetically, and to avoid the cable(s) brushing the user's face in operation, it would normally be the case that the cable(s) would enter or join the HMD at the side or back of the HMD (relative to the orientation of the user's head when worn in normal operation). Accordingly, the position of the cables relative to the HMD in FIG. 1 should be treated merely as a schematic representation.

Accordingly, the arrangement of FIG. 1 provides an example of a head-mountable display system comprising a frame to be mounted onto an observer's head, the frame defining one or two eye display positions which, in use, are positioned in front of a respective eye of the observer and a display element mounted with respect to each of the eye display positions, the display element providing a virtual image of a video display of a video signal from a video signal source to that eye of the observer.

FIG. 1 shows just one example of an HMD. Other formats are possible: for example an HMD could use a frame more similar to that associated with conventional eyeglasses, namely a substantially horizontal leg extending back from the display portion to the top rear of the user's ear, possibly curling down behind the ear. In other (not full immersion) examples, the user's view of the external environment may not in fact be entirely obscured; the displayed images could be arranged so as to be superposed (from the user's point of view) over the external environment. An example of such an arrangement will be described below with reference to FIG. 4.

Figure 2:
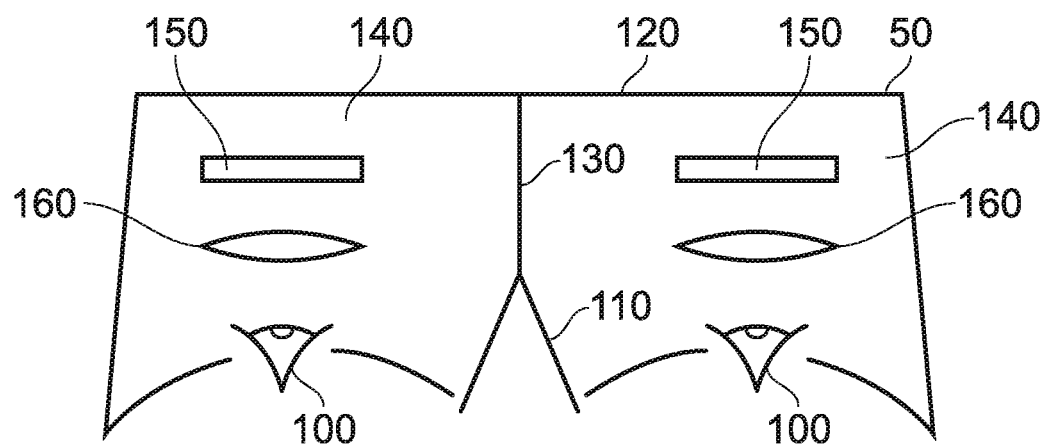
FIG. 2 is a schematic plan view of an HMD.

In the example of FIG. 1, a separate respective display is provided for each of the user's eyes. A schematic plan view of how this is achieved is provided as FIG. 2, which illustrates the positions 100 of the user's eyes and the relative position 110 of the user's nose. The display portion 50, in schematic form, comprises an exterior shield 120 to mask ambient light from the user's eyes and an internal shield 130 which prevents one eye from seeing the display intended for the other eye. The combination of the user's face, the exterior shield 120 and the interior shield 130 form two compartments 140, one for each eye. In each of the compartments there is provided a display element 150 and one or more optical elements 160. The way in which the display element and the optical element(s) cooperate to provide a display to the user will be described with reference to FIG. 3.

Figure 3:
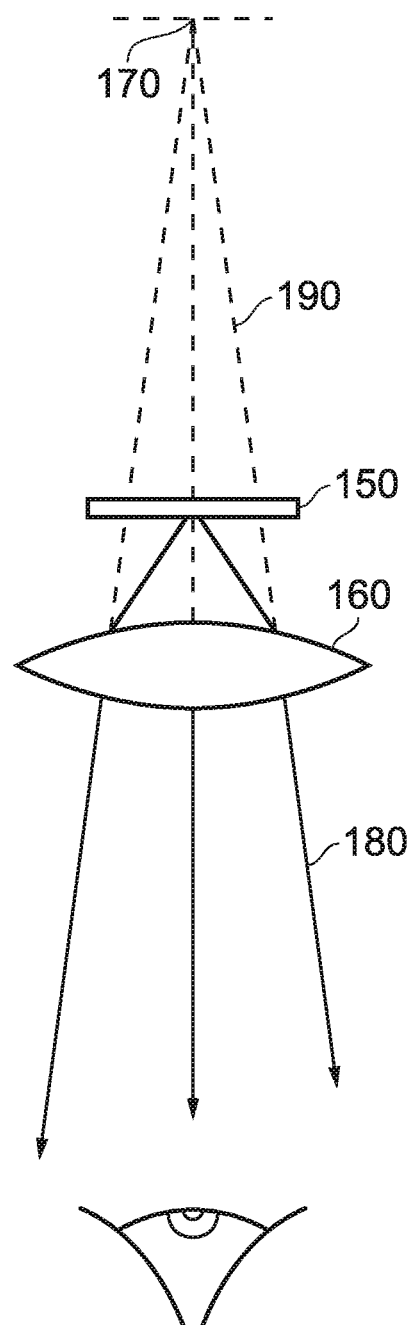
FIG. 3 schematically illustrates the formation of a virtual image by an HMD.

Referring to FIG. 3, the display element 150 generates a displayed image which is (in this example) refracted by the optical elements 160 (shown schematically as a convex lens but which could include compound lenses or other elements) so as to generate a virtual image 170 which appears to the user to be larger than and significantly further away than the real image generated by the display element 150. As an example, the virtual image may have an apparent image size (image diagonal) of more than 1 m and may be disposed at a distance of more than 1 m from the user's eye (or from the frame of the HMD). In general terms, depending on the purpose of the HMD, it is desirable to have the virtual image disposed a significant distance from the user. For example, if the HMD is for viewing movies or the like, it is desirable that the user's eyes are relaxed during such viewing, which requires a distance (to the virtual image) of at least several metres. In FIG. 3, solid lines (such as the line 180) are used to denote real optical rays, whereas broken lines (such as the line 190) are used to denote virtual rays.

Figure 4:
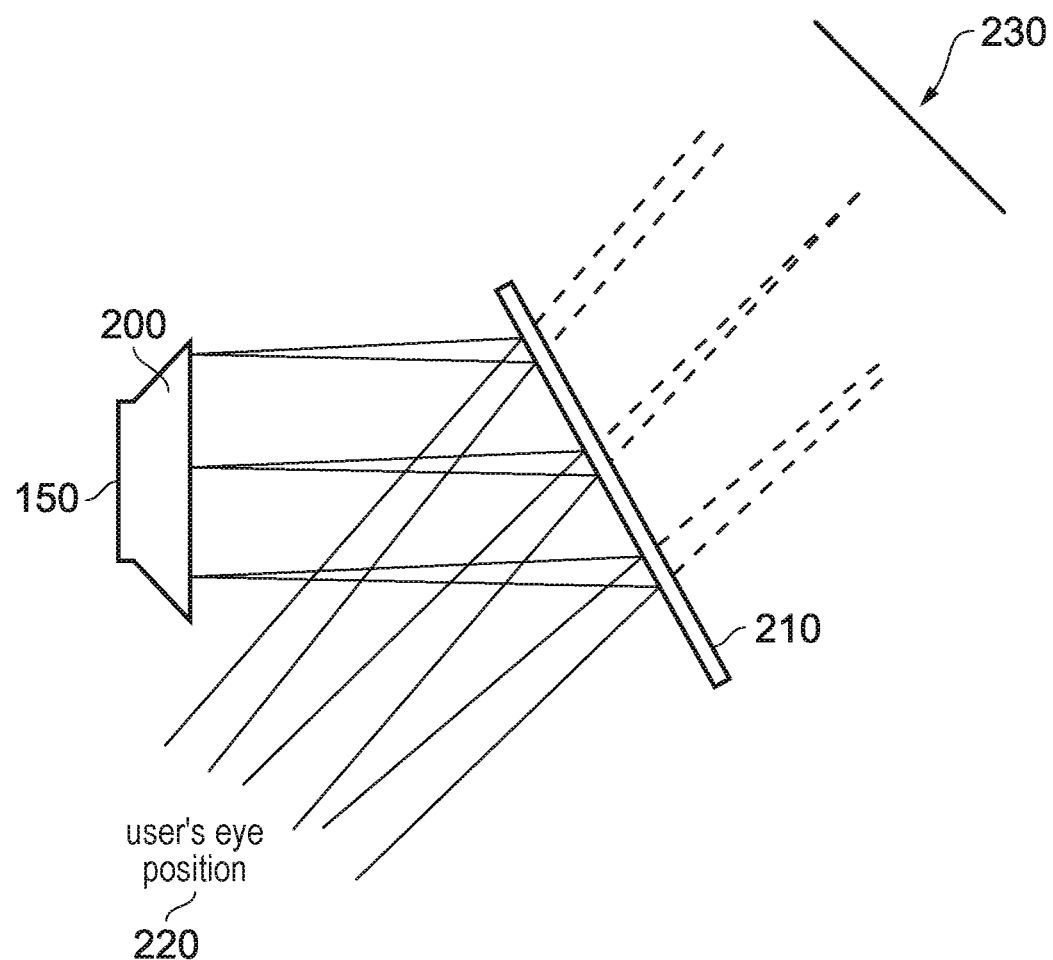
FIG. 4 schematically illustrates another type of display for use in an HMD.

An alternative arrangement is shown in FIG. 4. This arrangement may be used where it is desired that the user's view of the external environment is not entirely obscured. However, it is also applicable to HMDs in which the user's external view is wholly obscured. In the arrangement of FIG. 4, the display element 150 and optical elements 200 cooperate to provide an image which is projected onto a mirror 210, which deflects the image towards the user's eye position 220. The user perceives a virtual image to be located at a position 230 which is in front of the user and at a suitable distance from the user.

In the case of an HMD in which the user's view of the external surroundings is entirely obscured, the mirror 210 can be a substantially 100% reflective mirror. The arrangement of FIG. 4 then has the advantage that the display element and optical elements can be located closer to the centre of gravity of the user's head and to the side of the user's eyes, which can produce a less bulky HMD for the user to wear. Alternatively, if the HMD is designed not to completely obscure the user's view of the external environment, the mirror 210 can be made partially reflective so that the user sees the external environment, through the mirror 210, with the virtual image superposed over the real external environment.

Figure 5:
FIG. 5 schematically illustrates a pair of stereoscopic images.

In the case where separate respective displays are provided for each of the user's eyes, it is possible to display stereoscopic images. An example of a pair of stereoscopic images for display to the left and right eyes is shown in FIG. 5. The images exhibit a lateral displacement relative to one another, with the displacement of image features depending upon the (real or simulated) lateral separation of the cameras by which the images were captured, the angular convergence of the cameras and the (real or simulated) distance of each image feature from the camera position.

Note that the lateral displacements in FIG. 5 could in fact be the other way round, which is to say that the left eye image as drawn could in fact be the right eye image, and the right eye image as drawn could in fact be the left eye image. This is because some stereoscopic displays tend to shift objects to the right in the right eye image and to the left in the left eye image, so as to simulate the idea that the user is looking through a stereoscopic window onto the scene beyond. However, some HMDs use the arrangement shown in FIG. 5 because this gives the impression to the user that the user is viewing the scene through a pair of binoculars. The choice between these two arrangements is at the discretion of the system designer.

In some situations, an HMD may be used simply to view movies and the like. In this case, there is no change required to the apparent viewpoint of the displayed images as the user turns the user's head, for example from side to side. In other uses, however, such as those associated with virtual reality (VR) or augmented reality (AR) systems, the user's viewpoint needs to track movements with respect to a real or virtual space in which the user is located.

As mentioned above, in some uses of the HMD, such as those associated with virtual reality (VR) or augmented reality (AR) systems, the user's viewpoint needs to track movements with respect to a real or virtual space in which the user is located.

This tracking is carried out by detecting motion of the HMD and varying the apparent viewpoint of the displayed images so that the apparent viewpoint tracks the motion. The detection may be performed using any suitable arrangement (or a combination of such arrangements). Examples include the use of hardware motion detectors (such as accelerometers or gyroscopes), external cameras operable to image the HMD, and outwards-facing cameras mounted onto the HMD.

Turning to gaze tracking in such an arrangement, FIG. 6 schematically illustrates two possible arrangements for performing eye tracking on an HMD. The cameras provided within such arrangements may be selected freely so as to be able to perform an effective eye-tracking method. In some existing arrangements, visible light cameras are used to capture images of a user's eyes. Alternatively, infra-red (IR) cameras are used so as to reduce interference either in the captured signals or with the user's vision should a corresponding light source be provided, or to improve performance in low-light conditions.

Figure 6A:
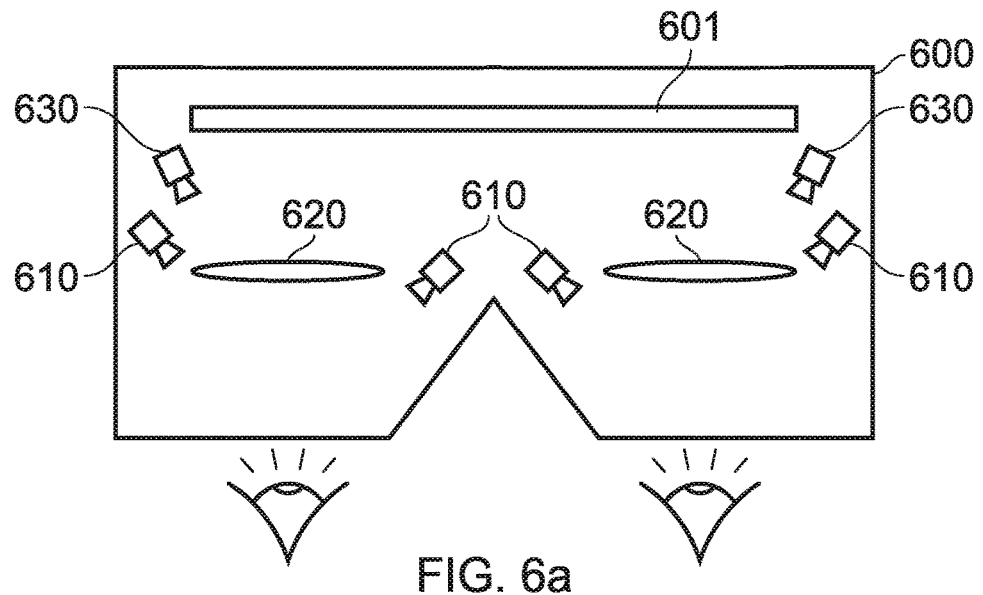
FIG. 6a schematically illustrates a plan view of an HMD.

FIG. 6a shows an example of a gaze tracking arrangement in which the cameras are arranged within an HMD so as to capture images of the user's eyes from a short distance. This may be referred to as near-eye tracking, or head-mounted tracking.

In this example, an HMD 600 (with a display element 601) is provided with cameras 610 that are each arranged so as to directly capture one or more images of a respective one of the user's eyes using an optical path that does not include the lens 620. This may be advantageous in that distortion in the captured image due to the optical effect of the lens is able to be avoided. Four cameras 610 are shown here as examples of possible positions that eye-tracking cameras may provided, although it should be considered that any number of cameras may be provided in any suitable location so as to be able to image the corresponding eye effectively. For example, only one camera may be provided per eye or more than two cameras may be provided for each eye.

However it is considered that in a number of embodiments it is advantageous that the cameras are instead arranged so as to include the lens 620 in the optical path used to capture images of the eye. Examples of such positions are shown by the cameras 630. While this may result in processing being required to enable suitably accurate tracking to be performed, due to the deformation in the captured image due to the lens, this may be performed relatively simply due to the fixed relative positions of the corresponding cameras and lenses. An advantage of including the lens within the optical path may be that of simplifying the physical constraints upon the design of an HMD, for example.

Figure 6B:
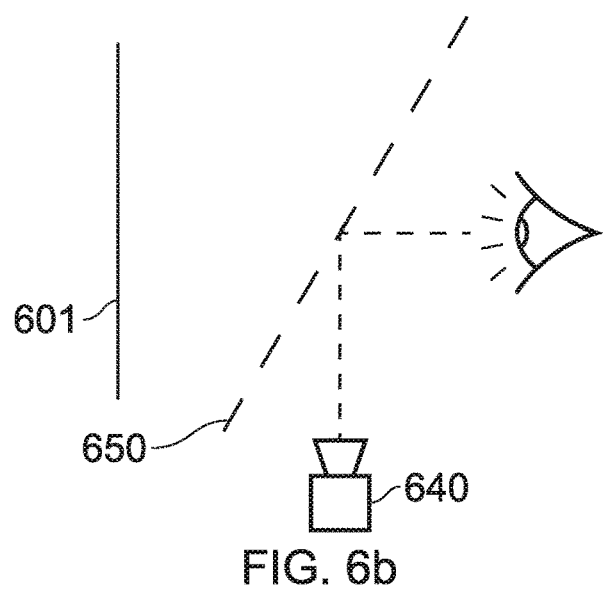
FIG. 6b schematically illustrates a near-eye tracking arrangement.

FIG. 6b shows an example of a gaze tracking arrangement in which the cameras are instead arranged so as to indirectly capture images of the user's eyes. Such an arrangement may be particularly suited to use with IR or otherwise non-visible light sources, as will be apparent from the below description.

FIG. 6b includes a mirror 650 arranged between a display 601 and the viewer's eye (of course, this can be extended to or duplicated at the user's other eye as appropriate). For the sake of clarity, any additional optics (such as lenses) are omitted in this Figure—it should be appreciated that they may be present at any suitable position within the depicted arrangement. The mirror 650 in such an arrangement is selected so as to be partially transmissive; that is, the mirror 650 should be selected so as to enable the camera 640 to obtain an image of the user's eye while the user views the display 601. One method of achieving this is to provide a mirror 650 that is reflective to IR wavelengths but transmissive to visible light—this enables IR light used for tracking to be reflected from the user's eye towards the camera 640 while the light emitted by the display 601 passes through the mirror uninterrupted.

Such an arrangement may be advantageous in that the cameras may be more easily arranged out of view of the user, for instance. Further to this, improvements to the accuracy of the eye tracking may be obtained due to the fact that the camera captures images from a position that is effectively (due to the reflection) along the axis between the user's eye and the display.

Figure 7:
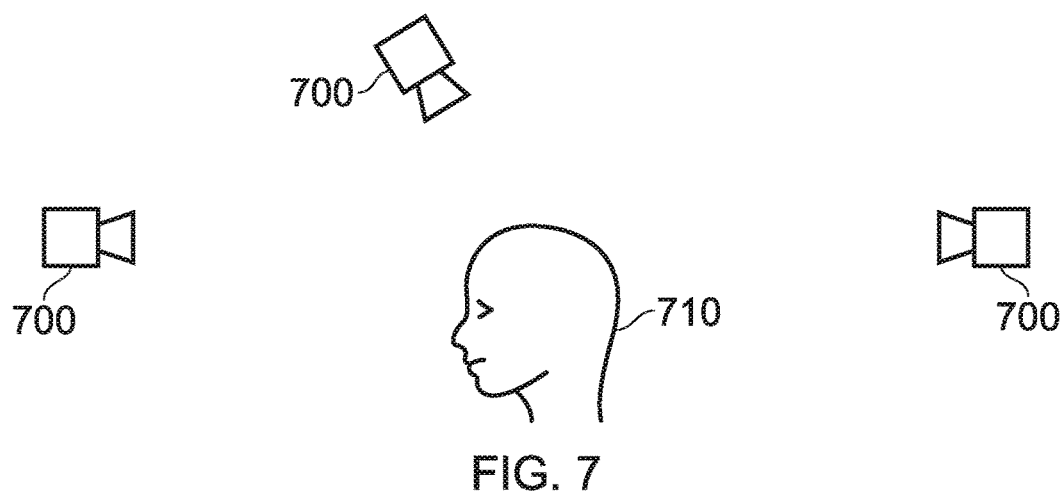
FIG. 7 schematically illustrates a remote tracking arrangement.

Of course, eye-tracking arrangements need not be implemented in a head-mounted or otherwise near-eye fashion as has been described above. For example, FIG. 7 schematically illustrates a system in which a camera is arranged to capture images of the user from a distance; this distance may vary during tracking, and may take any value in dependence upon the parameters of the tracking system. For example, this distance may be thirty centimetres, a metre, five metres, ten metres, or indeed any value so long as the tracking is not performed using an arrangement that is affixed to the user's head.

In FIG. 7, an array of cameras 700 is provided that together provide multiple views of the user 710. These cameras are configured to capture information identifying at least the direction in which a user's 710 eyes are focused, using any suitable method. For example, IR cameras may be utilised to identify reflections from the user's 710 eyes. An array of cameras 700 may be provided so as to provide multiple views of the user's 710 eyes at any given time, or may be provided so as to simply ensure that at any given time at least one camera 700 is able to view the user's 710 eyes. It is apparent that in some use cases it may not be necessary to provide such a high level of coverage and instead only one or two cameras 700 may be used to cover a smaller range of possible viewing directions of the user 710.

Of course, the technical difficulties associated with such a long-distance tracking method may be increased; higher resolution cameras may be required, as may stronger light sources for generating IR light, and further information (such as head orientation of the user) may need to be input to determine a focus of the user's gaze. The specifics of the arrangement may be determined in dependence upon a required level of robustness, accuracy, size, and/or cost, for example, or any other design consideration.

Despite technical challenges including those discussed above, such tracking methods may be considered beneficial in that they allow a greater range of interactions for a user—rather than being limited to HMD viewing, gaze tracking may be performed for a viewer of a television, for instance.

Rather than varying only in the location in which cameras are provided, eye-tracking arrangements may also differ in where the processing of the captured image data to determine tracking data is performed.

Figure 8:
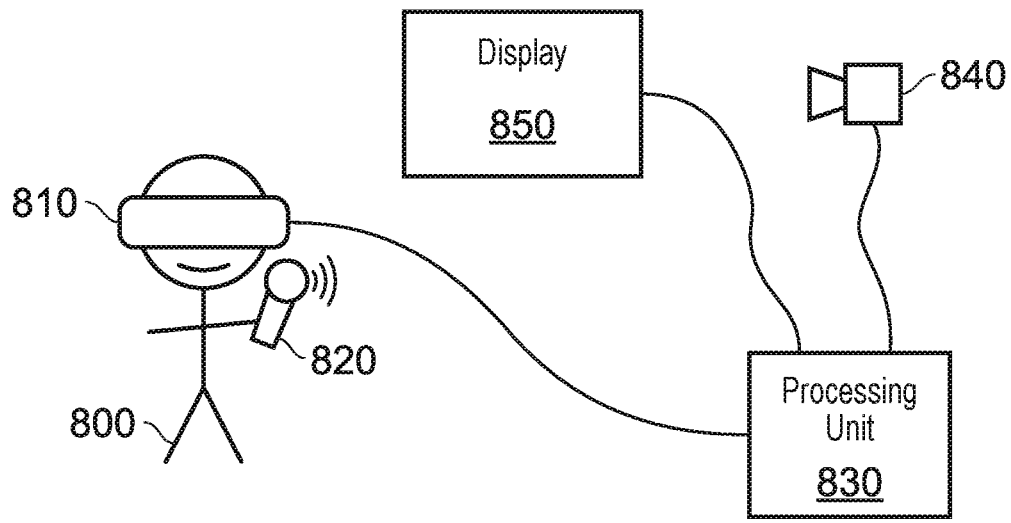
FIG. 8 schematically illustrates a gaze tracking environment.

FIG. 8 schematically illustrates an environment in which an eye-tracking process may be performed. In this example, the user 800 is using an HMD 810 that is associated with the processing unit 830, such as a games console, with the peripheral 820 allowing a user 800 to input commands to control the processing. The HMD 810 may perform eye tracking in line with an arrangement exemplified by FIG. 6a or 6b, for example—that is, the HMD 810 may comprise one or more cameras operable to capture images of either or both of the user's 800 eyes. The processing unit 830 may be operable to generate content for display at the HMD 810; although some (or all) of the content generation may be performed by processing units within the HMD 810.

The arrangement in FIG. 8 also comprises a camera 840, located outside of the HMD 810, and a display 850. In some cases, the camera 840 may be used for performing tracking of the user 800 while using the HMD 810, for example to identify body motion or a head orientation. The camera 840 and display 850 may be provided as well as or instead of the HMD 810; for example these may be used to capture images of a second user and to display images to that user while the first user 800 uses the HMD 810, or the first user 800 may be tracked and view content with these elements instead of the HMD 810. That is to say, the display 850 may be operable to display generated content provided by the processing unit 830 and the camera 840 may be operable to capture images of one or more users' eyes to enable eye-tracking to be performed.

While the connections shown in FIG. 8 are shown by lines, this should of course not be taken to mean that the connections should be wired; any suitable connection method, including wireless connections such as wireless networks or Bluetooth®, may be considered suitable. Similarly, while a dedicated processing unit 830 is shown in FIG. 8 it is also considered that the processing may in some embodiments be performed in a distributed manner—such as using a combination of two or more of the HMD 810, one or more processing units, remote servers (cloud processing), or games consoles.

The processing required to generate tracking information from captured images of the user's 800 eye or eyes may be performed locally by the HMD 810, or the captured images or results of one or more detections may be transmitted to an external device (such as a the processing unit 830) for processing. In the former case, the HMD 810 may output the results of the processing to an external device for use in an image generation process if such processing is not performed exclusively at the HMD 810. In embodiments in which the HMD 810 is not present, captured images from the camera 840 are output to the processing unit 830 for processing.

Figure 9:
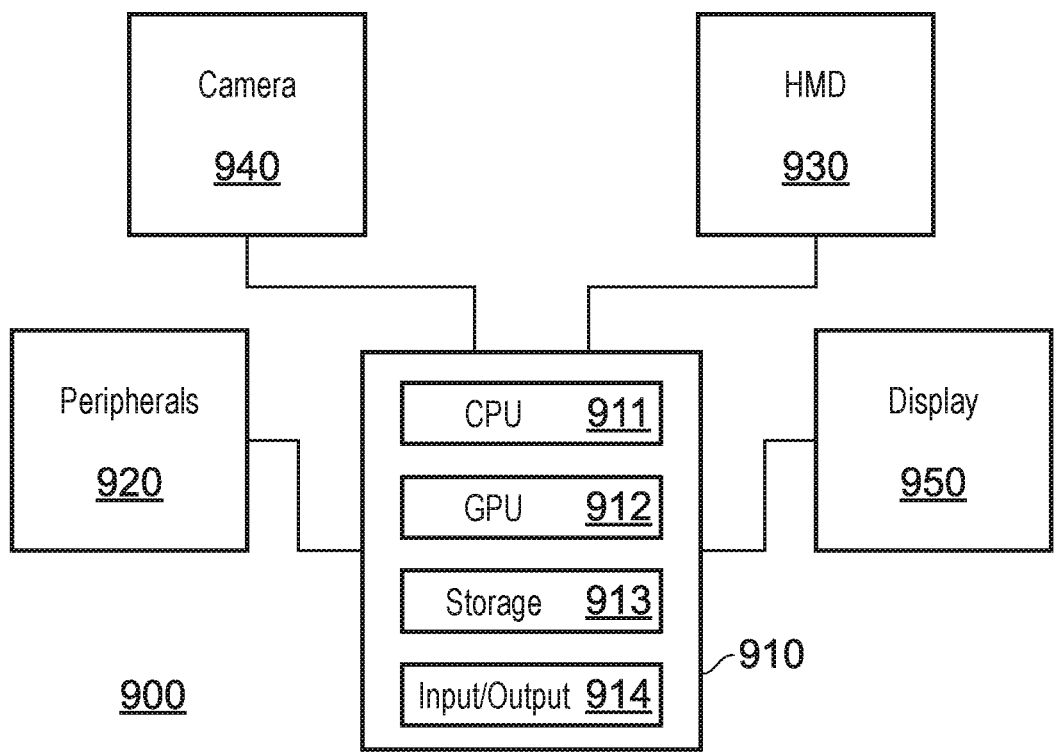
FIG. 9 schematically illustrates a gaze tracking system.

FIG. 9 schematically illustrates a system for performing one or more eye tracking processes, for example in an embodiment such as that discussed above with reference to FIG. 8. The system 900 comprises a processing device 910, one or more peripherals 920, an HMD 930, a camera 940, and a display 950. Of course, not all elements need be present within the system 900 in a number of embodiments—for instance, if the HMD 930 is present then it is considered that the camera 940 may be omitted as it is unlikely to be able to capture images of the user's eyes.

As shown in FIG. 9, the processing device 910 may comprise one or more of a central processing unit (CPU) 911, a graphics processing unit (GPU) 912, storage (such as a hard drive, or any other suitable data storage medium) 913, and an input/output 914. These units may be provided in the form of a personal computer, a games console, or any other suitable processing device.

For example, the CPU 911 may be configured to generate tracking data from one or more input images of the user's eyes from one or more cameras, or from data that is indicative of a user's eye direction. This may be data that is obtained from processing images of the user's eye at a remote device, for example. Of course, should the tracking data be generated elsewhere then such processing would not be necessary at the processing device 910.

The GPU 912 may be configured to generate content for display to the user on which the eye tracking is being performed. In some embodiments, the content itself may be modified in dependence upon the tracking data that is obtained—an example of this is the generation of content in accordance with a foveal rendering technique. Of course, such content generation processes may be performed elsewhere—for example, an HMD 930 may have an on-board GPU that is operable to generate content in dependence upon the eye tracking data.

The storage 913 may be provided so as to store any suitable information. Examples of such information include program data, content generation data, and eye tracking model data. In some cases, such information may be stored remotely such as on a server, and as such a local storage 913 may not be required—the discussion of the storage 913 should therefore be considered to refer to local (and in some cases removable storage media) or remote storage.

The input/output 914 may be configured to perform any suitable communication as appropriate for the processing device 910. Examples of such communication include the transmission of content to the HMD 930 and/or display 950, the reception of eye-tracking data and/or images from the HMD 930 and/or the camera 940, and communication with one or more remote servers (for example, via the internet).

As discussed above, the peripherals 920 may be provided to allow a user to provide inputs to the processing device 910 in order to control processing or otherwise interact with generated content. This may be in the form of button presses or the like, or alternatively via tracked motion to enable gestures to be used as inputs.

The HMD 930 may comprise a number of sub-elements, which have been omitted from FIG. 9 for the sake of clarity. Of course, the HMD 930 should comprise a display unit operable to display images to a user. In addition to this, the HMD 930 may comprise any number of suitable cameras for eye tracking (as discussed above), in addition to one or more processing units that are operable to generate content for display and/or generate eye tracking data from the captured images.

The camera 940 and display 950 may be configured in accordance with the discussion of the corresponding elements above with respect to FIG. 8.

Turning to the image capture process upon which the eye tracking is based, examples of different cameras are discussed. The first of these is a standard camera, which captures a sequence of images of the eye that may be processed to determine tracking information. The second is that of an event camera, which instead generates outputs in accordance with observed changes in brightness.

It is more common to use standard cameras in such tracking arrangements, given that they are widely available and often relatively cheap to produce. 'Standard cameras' here refer to cameras which capture images of the environment at predetermined intervals which can be combined to generate video content. For example, a typical camera of this type may capture thirty images (frames) each second, and these images may be output to a processing unit for feature detection or the like to be performed so as to enable tracking of the eye.

Such a camera comprises a light-sensitive array that is operable to record light information during an exposure time, with the exposure time being controlled by a shutter speed (the speed of which dictates the frequency of image capture). The shutter may be configured as a rolling shutter (line-by-line reading of the captured information) or a global shutter (reading the captured information of the whole frame simultaneously), for example.

However, in some arrangements it may be considered advantageous to instead use an event camera, which may also be referred to as a dynamic vision sensor. Such cameras do not require a shutter as described above, and instead each element of the light-sensitive array (often referred to as a pixel) is configured to output a signal at any time a threshold brightness change is observed. This means that images are not output in the traditional sense—however an image reconstruction algorithm may be applied that is able to generate an image from the signals output by an event camera.

While there is an increased computational complexity for generating an image from such data, the output of the event camera can be used for tracking without any image generation. One example of how this is performed is that of using an IR-sensitive event camera; when imaged using IR light, the pupil of the human eye displays a much higher level of brightness than the surrounding features. By selecting an appropriate threshold brightness, the motion of the pupil would be expected to trigger events (and corresponding outputs) at the sensor.

Independent of the type of camera that is selected, in many cases it may be advantageous to provide illumination to the eye in order to obtain a suitable image. One example of this is the provision of an IR light source that is configured to emit light in the direction of one or both of the user's eyes; an IR camera may then be provided that is able to detect reflections from the user's eye in order to generate an image. IR light may be preferable as it is invisible to the human eye, and as such does not interfere with normal viewing of content by the user, but it is not considered to be essential. In some cases, the illumination may be provided by a light source that is affixed to the imaging device, while in other embodiments it may instead be that the light source is arranged away from the imaging device.

Figure 10:
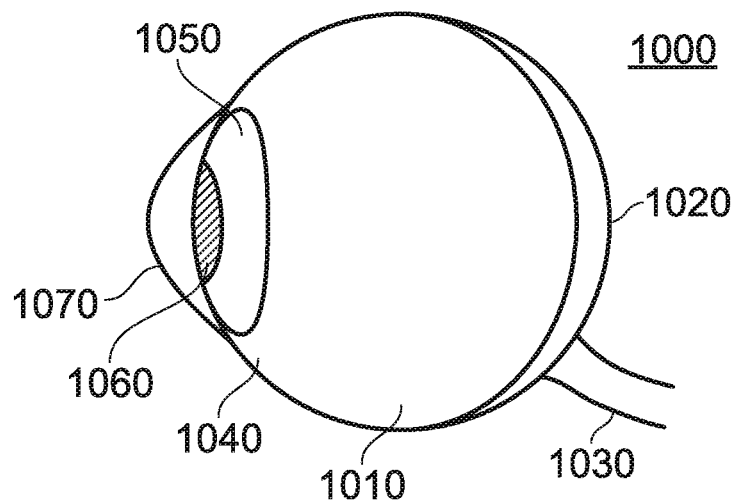
FIG. 10 schematically illustrates a human eye.

As suggested in the discussion above, the human eye does not have a uniform structure; that is, the eye is not a perfect sphere, and different parts of the eye have different characteristics (such as varying reflectance or colour). FIG. 10 shows a simplified side view of the structure of a typical eye 1000; this Figure has omitted features such as the muscles which control eye motion for the sake of clarity.

The eye 1000 is formed of a near-spherical structure filled with an aqueous solution 1010, with a retina 1020 formed on the rear surface of the eye 1000. The optic nerve 1030 is connected at the rear of the eye 1000. Images are formed on the retina 1020 by light entering the eye 1000, and corresponding signals carrying visual information are transmitted from the retina 1020 to the brain via the optic nerve 1030.

Turning to the front surface of the eye 1000, the sclera 1040 (commonly referred to as the white of the eye) surrounds the iris 1050. The iris 1050 controls the size of the pupil 1060, which is an aperture through which light enters the eye 1000. The iris 1050 and pupil 1060 are covered by the cornea 1070, which is a transparent layer which can refract light entering the eye 1000. The eye 1000 also comprises a lens (not shown) that is present behind the iris 1050 that may be controlled to adjust the focus of the light entering the eye 1000.

Figure 11:
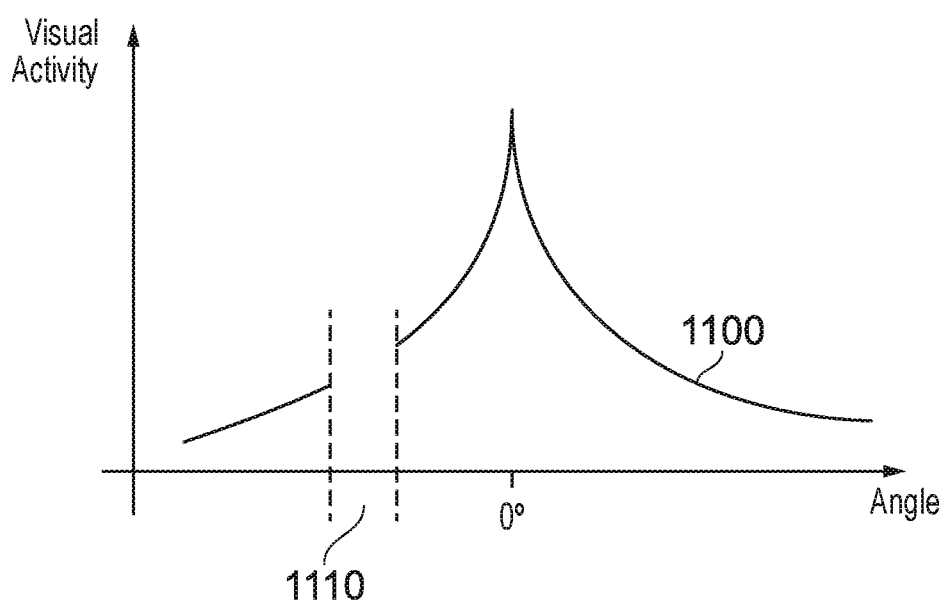
FIG. 11 schematically illustrates a graph of human visual acuity.

The structure of the eye is such that there is an area of high visual acuity (the fovea), with a sharp drop off either side of this. This is illustrated by the curve 1100 of FIG. 11, with the peak in the centre representing the foveal region. The area 1110 is the 'blind spot'; this is an area in which the eye has no visual acuity as it corresponds to the area where the optic nerve meets the retina. The periphery (that is, the viewing angles furthest from the fovea) is not particularly sensitive colour or detail, and instead is used to detect motion.

As has been discussed above, foveal rendering is a rendering technique that takes advantage of the relatively small size (around 2.5 degrees) of the fovea and the sharp fall-off in acuity outside of that.

The eye undergoes a large amount of motion during viewing, and this motion may be categorised into one of a number of categories.

Saccades, and on a smaller scale micro-saccades, are identified as fast motions in which the eyes rapidly move between different points of focus (often in a jerky fashion). This may be considered as ballistic motion, in that once the movement has been initiated it cannot be altered. Saccades are often not conscious eye motions, and instead are performed reflexively to survey an environment. Saccades may last up to two hundred milliseconds, depending on the distance rotated by the eye, but may be as short as twenty milliseconds. The speed of a saccade is also dependent upon the total rotation angle; typical speeds may be between two hundred and five hundred degrees per second.

'Smooth pursuit' refers to a slower movement type than a saccade. Smooth pursuit is generally associated with a conscious tracking of a point of focus by a viewer, and is performed so as to maintain the position of a target within (or at least substantially within) the foveal region of the viewer's vision. This enables a high-quality view of a target of interest to be maintained in spite of motion. If the target moves too fast, then smooth pursuit may instead require a number of saccades in order to keep up; this is because smooth pursuit has a lower maximum speed, in the region of thirty degrees per second.

The vestibular-ocular reflex is a further example of eye motion. The vestibular-ocular reflex is the motion of the eyes that counteracts head motion; that is, the motion of the eyes relative to the head that enables a person to remain focused on a particular point despite moving their head.

Another type of motion is that of the vergence accommodation reflex. This is the motion that causes the eyes to rotate to converge at a point, and the corresponding adjustment of the lens within the eye to cause that point to come into focus.

Further eye motions that may be observed as a part of a gaze tracking process are those of blinks or winks, in which the eyelid covers the eyes of the user. Such motions may be reflexive or intentional, and can often interfere with eye tracking as they will obscure vision of the eye, and the eye is often not stationary during such a motion.

As noted above, in some arrangements it is preferable that a distance (or remote) gaze tracking method is employed. An example of such an arrangement is discussed above with reference to FIG. 7. Gaze tracking using such arrangements may be problematic in that a lower-quality tracking is provided relative to arrangements that are able to capture images from locations closer to the user's eyes. In some cases, this may be offset by increasing the resolution of a camera performing the tracking—but this may require a significant increase in processing resources for performing the tracking and can therefore introduce a latency and/or create a substantial processing burden on the tracking device.

Embodiments of the present disclosure seek to address such problems, and generally to provide an improved gaze tracking arrangement that enables effective and/or efficient gaze tracking to be performed at distance from the user's eyes. This is achieved by providing a dual-tracking method according to any one or more of the following embodiments that are discussed in this disclosure.

Figure 12:
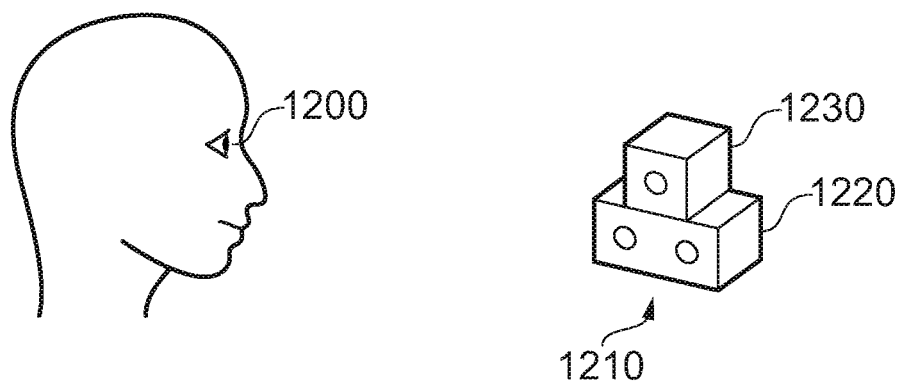
FIG. 12 schematically illustrates a remote gaze tracking system.

In a number of embodiments of the present disclosure, a pair of cameras is provided for capturing images of the user. An example of such an arrangement is shown in FIG. 12; a camera arrangement 1210 is shown that comprises a first camera 1220 and a second camera 1230. The user's eye is indicated by the reference sign 1200. The camera arrangement 1210 may be located at a games console or a television that is being operated in dependence upon the user's gaze, for example; however the location may be selected freely so long as images of the user may be captured by the arrangement 1210. Further examples of appropriate configurations are discussed below; the arrangement of FIG. 12 is not intended to be limiting as to the arrangement of hardware elements or their specific properties.

It is considered that the first camera 1220 is selected to have a larger field of view than the second camera 1230; that is, the first camera 1220 is operable to capture an image of a larger portion of the environment than the second camera 1230. This may be achieved by an appropriate selection of lenses for each of the cameras, or an appropriate selection of imaging sensors, for example. An example of appropriate fields of view may be that of the first camera 1220 being able to image an angular region of seventy degrees or more (it may comprise a wide-angle lens, in some embodiments) while the second camera 1230 is operable to image the user's face only. Of course, this functionality may be determined for a suitable reference distance (such as based upon an expected distance between the user and the camera when in use). It is also considered that the field of view of a camera may be able to be modified during use to ensure the correct functionality; for example, with a device comprising multiple lenses or an arrangement capable of focusing the image capture area.

The purpose of this arrangement is to enable the first camera 1220 to capture an image of the user within the environment so as to enable the targeting of the second camera 1230 at a smaller region (such as the user's face). In practice, this enables a more detailed image of the user's eyes to be obtained than if the first camera 1220 were used alone. This can enable tracking to be performed with a greater degree of accuracy and precision, in many cases. Throughout this description, references to the 'first camera 1220' should be regarded as referring to a camera in any suitable arrangement which is operable to capture wider field of view images, while references to a 'second camera 1230' should similarly be regarded as referring to a camera which is operable to capture images for the gaze tracking itself.

Figure 13:
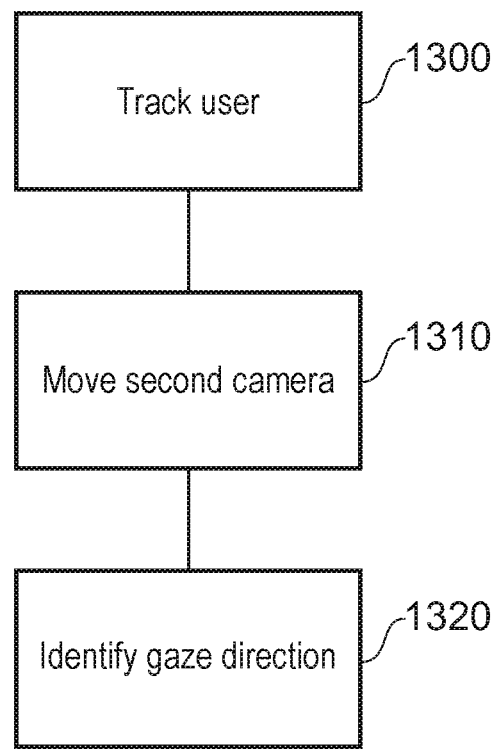
FIG. 13 schematically illustrates a gaze tracking method.

FIG. 13 illustrates an exemplary method for performing a gaze tracking process using such an arrangement. Of course, other steps may be added to the method as appropriate, and the process should not be limited to the hardware arrangements shown in FIG. 12 but instead may be applicable to any suitable configuration of imaging hardware or the like.

At a step 1300, tracking is performed to identify the location of a user. This may be the location of the user's head, in some embodiments, and/or one or both of the user's eyes—although in some cases it may be appropriate to track another part of the user's body and to simply infer the position of the user's head and/or eyes based upon the location of that body part. An example of this may be in the case that a user is identified by a badge or other graphic affixed to their chest, which can be identified as being a fixed distance (or substantially fixed) from the user's head.

Such an embodiment is also an example of a case when a predetermined marker, such as an AR marker or any other recognisable imagery, may be used to simplify the tracking process performed with the first camera. Of course, such a marker may be located anywhere on the user as appropriate, and may take any suitable form; a distinctive headband or neckwear are both examples of suitable alternatives, as is the detection of a user's glasses or the like.

Of course, any suitable image processing techniques may be used to perform the identification of the location of the user or any other element that is to be located. Pattern recognition and edge detection are two examples of steps that may be performed, although this should not be regarded as being limiting in any way. Any of a number of image processing techniques may be selected, with the purpose of being able to identify a particular element or object within the captured images.

In addition to image processing techniques, predictive methods may also be employed to identify a likely location of the user or an expected motion.

At a step 1310, the position and/or orientation of the second camera 1230 is modified so as to cause it to be directed towards the user's head or, in some embodiments, more specifically towards the user's eyes. This repositioning and/or reorientation is therefore performed in dependence upon the tracking performed using the first camera 1220 in step 1300, which is operable to identify the location (directly or indirectly) of the user's head and/or eyes.

This repositioning/reorientation may be performed in any suitable manner; for example, the whole of the camera apparatus may be moved. Alternatively, or in addition, the repositioning/reorientation may be performed my moving one or more mirrors and/or lenses associated with the camera so as to modify the portion of the environment that is imaged by the camera. That is to say that the purpose of the step 1310 is to cause the field of view of the second camera to be modified so as to be able to obtain images of at least one or the user's eyes.

At a step 1320, tracking of the user's gaze direction is performed using images obtained from the second camera 1220 (that is, the camera that is repositioned or reoriented in step 1310). Any suitable image-based process may be used; for instance, one or both of the user's pupils may be identified in the captured images in order to identify a gaze direction.

Of course, any suitable ordering of these steps may be applied in practice; for example, steps 1300 and 1310 may be performed sequentially at any suitable rate—this rate may be higher than or otherwise different to the rate at which step 1320 is performed. The relative rates at which the steps are performed may be based upon technical parameters, for example, such as the relative field of view of the cameras that are used.

The above method therefore illustrates an example of a process by which two tracking processes are used in combination to identify the gaze direction of a user.

While the above discussion has focused on an arrangement which utilises only two cameras, it is considered that instead a group of cameras may be used. For example, in FIG. 14 it is shown that several camera arrangements 1400 are provided that surround a user 1410; this may enable a more effective tracking of the user's gaze direction in that it is possible to capture images of the user's eyes even if the user 1410 turns away from a camera. Each of the cameras 1400 may correspond to the camera arrangement 1210 of FIG. 12, or either of the cameras 1220 or 1230 as appropriate for a particular use. For example, opposing pairs of the cameras 1400 may correspond to the same one of the cameras 1220 and 1230 such that a pair of each of the cameras is provided in the group of cameras in FIG. 14.

Figure 15:
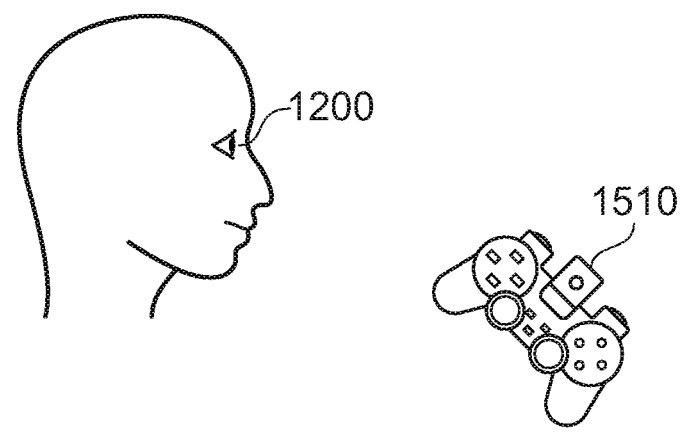
FIG. 15 schematically illustrates a gaze tracking system comprising a non-stationary camera unit.

FIG. 15 provides an example of an arrangement in which one of the cameras does not have a fixed location. In this particular example a camera is formed as a part of a game controller, although this should merely be regarded as one possible way in which a camera may be provided without having a fixed location.

In FIG. 15, a remote camera 1500 is arranged so as to be able to capture images of at least the user's head within the environment so as to be able to enable a tracking of the user's head and/or eyes within the environment. A near camera 1510 is provided that is operable to capture images of at least one of the user's eyes 1200, based upon control in dependence upon the result of tracking performed using images captured by the remote camera 1500. To compare this to the arrangement of FIG. 12, the remote camera 1500 is comparable in function to the first camera 1220 while the near camera 1510 is comparable in function to the second camera 1230.

It would be apparent that as the near camera 1510 is formed as a part of a game controller (or otherwise affixed to), it would be subject to motion relative to the user's head during se by a user. This motion may be tracked in any suitable manner; examples include a tracking based upon images captured by the remote camera 1500, and the use of inertial sensors or other hardware motion detectors (for instance, accelerometers and/or gyroscopes). The location of the camera 1510, and indeed its orientation, may be tracked relative to the user's head and/or relative to the environment itself as appropriate. In some embodiments, it may be appropriate to use two or more tracking methods so as to increase the accuracy and/or precision of the tracking.

One advantage of such an arrangement is in that the increased proximity of the near camera 1510 to the user's eye or eyes 1200 relative to the second camera 1230 of FIG. 12 may enable a higher-quality image to be obtained. Further to this, the camera 1510 may be able to have a reduced cost due to a decrease in the technical requirements that may be envisaged for a suitable image capture process relative to that of the camera 1230 of FIG. 12.

Figure 14:
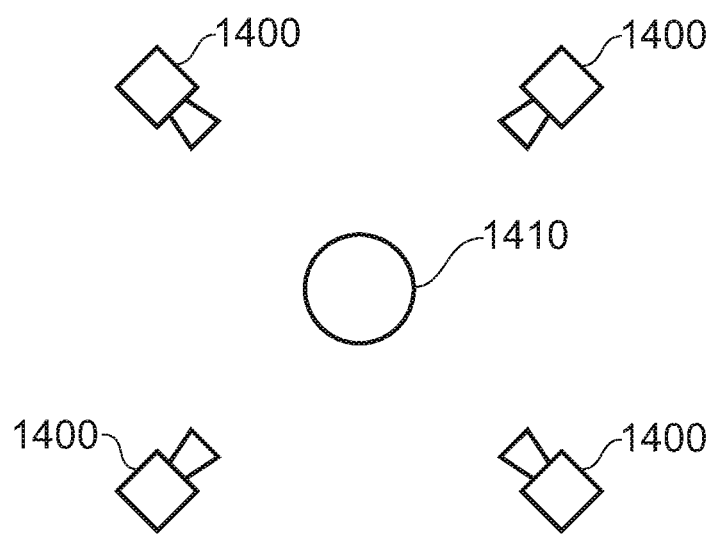
FIG. 14 schematically illustrates a remote gaze tracking system comprising multiple camera units.

Both the arrangements of FIG. 14 and FIG. 15 may be considered more suitable than the arrangement of FIG. 12 for multi-user gaze tracking arrangements; specific modifications (such as an increase in the number of cameras) may further aid this. For instance, in the example of FIG. 15, the camera 1500 may be operable to identify the location of each user's head and the orientation of a respective camera 1510 for each user may be modified in dependence upon the relevant identified location. With regards to FIG. 14, it is considered that an increase in the number of camera arrangements 1400 may be appropriate; the number itself may be selected freely, but should be selected so as to enable a suitable resilience to the user turning away from a camera as well as the number of users.

Of course, a number of other camera arrangements or modifications to the camera arrangements described above may also be considered. A selection of such modifications is described below; while each is presented separately, it is envisaged that any suitable combinations of the described modifications may also be implemented as appropriate.

One possible modification to the arrangements described above is that of the use of stereoscopic imaging by either or both of the cameras. This may enable an enhanced determination of the depth of elements within the captured image; for example, if the first camera 1220 uses a stereoscopic imaging process then it may be possible to more accurately identify the location of the user's head within the environment. Similarly, the use of a stereoscopic camera by the second camera 1230 may improve the gaze tracking as it may enable an improved estimation of the relative location of the camera and the user's eyes.

It may be advantageous in some embodiments to use more than two cameras in an analogous process for gaze tracking in which a more iterative approach is taken. For example, a first camera may be used to provide a large-scale tracking of the environment, such as to identify the number of users and an approximate location. One or more second cameras may then be used to identify a more accurate location of the user's heads based upon that tracking, with a third set of one or more cameras being used to perform the gaze tracking itself in dependence upon the more accurate identified location. The number of cameras or groups of cameras may be selected freely in such embodiments, and is not limited to only three groups.

In some embodiments, it may be considered advantageous to substitute at least the second camera 1230 with an arrangement comprising two or more cameras. For example, the second camera 1230 may instead comprise a pair of cameras that may be independently controlled so as to capture images of a respective one of the user's eyes. Alternatively, a greater number of cameras may be provided that each have a reduced range of motion, and images are used for tracking in dependence upon which camera is expected to be able to see the user's eye or eyes at a given time (for example, based upon a determined relative position/orientation of the cameras and the user's eye/eyes). Of course, similar modifications may also be made to the first camera 1220 so as to provide corresponding advantages.

While FIG. 15 illustrates an embodiment in which a second camera 1230 is formed as a part of, or affixed to, a game controller, numerous other examples of devices with which the second camera 1230 may be associated are envisaged. For example, a drone or other similar device could be used to provide a camera that is relatively near to the user's eyes; such a device could be controlled to move or rotate instead of (or in addition to) moving the camera itself to maintain an appropriate view of the user's eyes. A remote controlled device such as a car or helicopter may also be similarly appropriate, or any form of robotic device.

In addition to this, other handheld objects such as handheld consoles or controllers for devices other than games consoles (such as a wireless keyboard or a television remote) may be suitable devices with which to associate a second camera 1230. Other peripherals may also be examples of suitable devices, such as wristbands or gloves that are able to have cameras mounted upon them. Of course, other body parts may also be provided (directly or indirectly) with such cameras—objects associated with a user's hands are simply referenced here as an example.

As described with reference to FIG. 14, arrangements comprising multiple cameras are envisaged as being within the scope of the present disclosure. This should similarly apply to arrangements with non-fixed cameras too; for example, multiple peripherals or other devices may be equipped with cameras as appropriate. Any suitable combination of fixed and non-fixed cameras should be considered appropriate, with the motivation of obtaining a robust and reliable gaze tracking arrangement.

Figure 16:
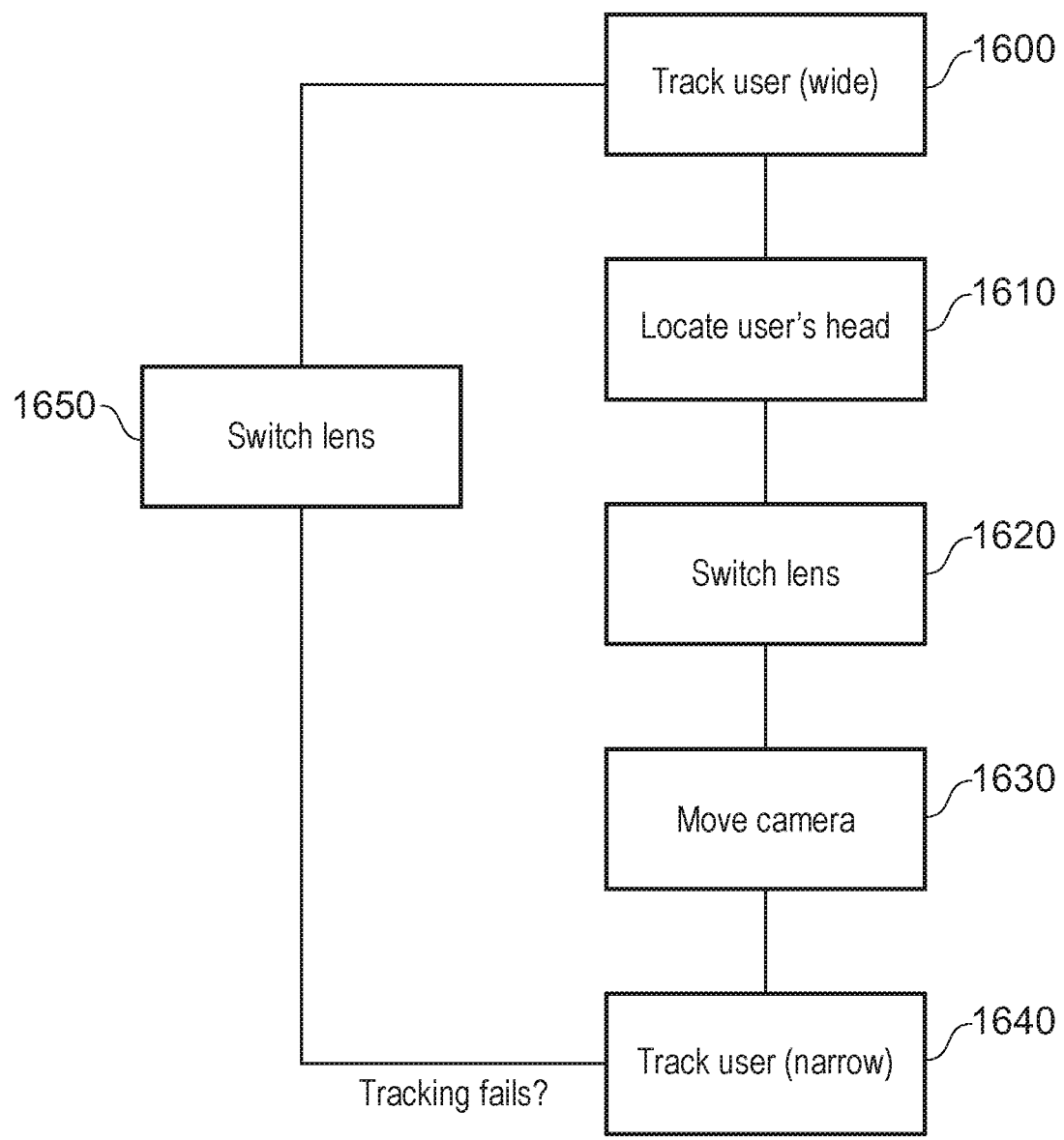
FIG. 16 schematically illustrates a remote gaze tracking method using a single camera.

In a number of embodiments, it is considered that a single camera with interchangeable lenses may be suitable for providing the functionality of both the first camera 1220 and the second camera 1230. An example of a suitable method for utilising such an arrangement is shown in FIG. 16.

At a step 1600, the tracking process is initiated using a lens associated with a suitably wide field of view so as to capture images of the user within the environment. In some embodiments, this may be a wide-angle or fisheye lens so as to provide a view of a substantial proportion of the environment. An example of a suitable field of view (as in the embodiments described above, for the camera 1220) is sixty degrees; although seventy degrees, eighty degrees, ninety degrees, or an even greater angular field of view may also be suitable. Of course, smaller fields of view may also be appropriate (such as fifty degrees or less), so long as it is possible to identify the location of a user in the environment. The selection of an appropriate field of view may be dependent upon a number of factors, including the expected distance of the user from the camera.

At a step 1610, the location of the user's head (or another suitable part of the user's body or the like, as discussed above) is identified from the images captured in step 1600. In some cases, a two-dimensional location may be sufficient but in some embodiments a three-dimensional location may be preferable. The location may be determined using any suitable image processing techniques, as described above.

At a step 1620, the camera is operable to switch to a second lens which offers a narrowed field of view relative to the first lens (that used in step 1600). As when considering the field of view of other cameras and/or lenses described elsewhere in this document, an appropriate field of view may be selected freely so as to ensure suitable functionality in particular arrangements or circumstances.

In some cases, the angular field of view of the second lens (as with the second camera 1230) may be twenty degrees (to give a specific example). Any other value may also be appropriate, however; smaller values such as fifteen degrees, ten degrees, five degrees, two degrees, or one degree (or any non-integer value) may be suitable sizes for focusing on a user's eye or eyes at particular distances. In general, an appropriate size may be determined in dependence upon an expected angular size of the user's eye or eyes during use (which is dependent upon the distance of the user from the camera). However, it is appreciated that other factors (such as resilience of the narrower field of view tracking to user motion) may suggest that a larger field of view may be more appropriate. These considerations and examples are, as noted earlier, applicable to the selection of a field of view for the second camera 1230 as discussed elsewhere in this document.

At a step 1630, the camera may be adjusted so as to be able to image the user's eye or eyes as appropriate. For instance, if the user's head is identified in step 1610 in the corner of the wide field of view image, then the camera may need to move or rotate so as to be able to image the user's eyes once the lens has been switched (and the field of view has therefore been narrowed).

At a step 1640, tracking is performed using the lens selected in step 1620; that is, tracking of one or both of the user's eyes is performed using a narrowed field of view. This tracking may be performed using any suitable image-based methods as described above.

During the tracking process of step 1640, it is considered that the adjustment of step 1630 may be performed with a suitable frequency or in response to detected motion so as to ensure that the tracked eye/eyes remain within view of the camera. This may be performed based upon the images captured by the camera, such that in some embodiments the position of the user's eye or eyes within the image (or any other suitable indicator) are able to be tracked to identify motion.

If the tracking in step 1640 fails, for example due to the camera losing sight of the user's eyes, the method proceeds to step 1650 in which the lens is switched back to the lens having a wider field of view. The process then returns to step 1600 to restart the tracking process from the beginning, in which the user is identified within the environment again.

It should be noted that in some embodiments, it the process may proceed to step 1650 with any suitable frequency or in response to any other suitable conditions so as to ensure that the tracking is reliable. For example, if tracking a single eye it may be possible that the camera mistakenly tracks the user's other eye (such as due to user or unintended camera motion). By reverting to the wider field of view to recalibrate the tracking, the impact of such errors may be at least somewhat mitigated.

While the above example discusses a camera with two lenses, it is of course possible that a greater number of lenses may be provided. This may enable a more refined tracking process to be performed; for example, by having one or more intermediate lenses between the widest and narrowest fields of view, it may be possible to select an appropriate lens to ensure tracking reliability in a given circumstance. For instance, a wider field of view lens may be seen as more appropriate when a user is more active, while a seated and relatively stationary user may be suitable for gaze tracking using a lens with a narrower field of view. These lenses may be switched between freely as appropriate within the context of the gaze tracking process.

In some embodiments, cameras may be provided that are able to capture images with different characteristics so as to increase the efficiency and/or effectiveness of the gaze tracking process.

A first example of this is the capturing of images of different resolutions by different cameras. For example, the first camera 1220 may be configured to capture lower resolution images than the second camera 1230. This may enable a faster image processing as a part of the tracking process, making the tracking more responsive without a significant impact on the accuracy as the camera that is used to image the eye is still of a high resolution. Alternatively, it may be considered in some embodiments that it is more appropriate for the first camera 1220 to be of a higher resolution. This may enable a more accurate locating of the user's eyes in the environment, and therefore a more accurate targeting of the second camera 1230.

An additional, or alternative, characteristic that may be modified is the wavelengths of light that are captured by the cameras. For example, either or both of the cameras 1220 and 1230 may be implemented so as to capture images using infrared light. This may be appropriate for the first camera 1220 so as to reduce the impact of light sources or colour interference in the environment that the user is in, for example. Of course, this may not be appropriate in all cases; for instance, when the first camera 1220 is used to capture images that are to be displayed to a user. In some cases, infrared light is considered to be advantageous in eye tracking and so this may be an appropriate choice for the second camera 1230. Of course, the skilled person would be free to select an appropriate wavelength (or range of wavelengths) to use in a particular arrangement, and would be free to select this for each camera as appropriate.

Other characteristics may also be selected freely for each camera as appropriate; it is considered that the cameras need not differ only in the field of view that is used for image capture.

In some cases, the tracking process may fail due to any of a number of factors. Here, failure means any situation in which either an incorrect (often by a greater-than-threshold amount) tracking result or no tracking result at all is generated. Examples of causes of this include sudden, significant motions by a user (causing the eye to move away from the field of view of the second camera 1230) or unintended motion of one or both of the cameras so as to cause the camera's field of view to move such that the user and/or the user's eye is no longer present in captured images.

While in such cases the tracking process may simply return to the first step (such as step 1300 of FIG. 13, or step 1600 of FIG. 16), one or more other processes may be implemented in the interim to reduce the impact of this loss of tracking information.

One example of such a process is that of predictive methods that are operable to determine (in dependence upon one or more input parameters) an expected gaze direction. Examples of suitable input parameters include a user profile (for instance, one that indicates a user's gaze habits), historical gaze tracking data, information about the content being viewed by a user, information about a device being interacted with by a user, and/or physical cues such as a user's head direction.

Another example is that of the use of a different input to replace gaze tracking as an indication of user input. For example, on a computer a cursor location may be an appropriate approximation of the user's gaze direction in a number of cases. Similarly, any other suitable inputs and/or indications may be used as appropriate.

Figure 17:
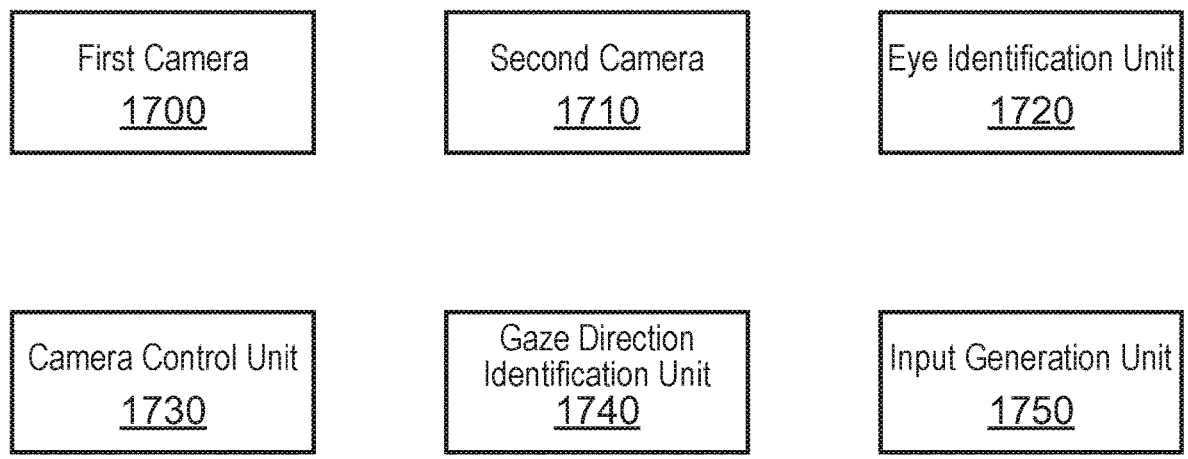
FIG. 17 schematically illustrates a gaze tracking system using two cameras with different fields of view.

FIG. 17 schematically illustrates a gaze tracking system operable to implement a number of the embodiments described above. This system comprises a first camera 1700, a second camera 1710, an eye identification unit 1720, a camera control unit 1730, a gaze direction identification unit 1740, and an input generation unit 1750. The order and/or location of each of these devices may be selected freely; for example, they may be all formed in a single unit or distributed in any suitable arrangement. Equally, other hardware elements may be present, and some may be omitted (such as the input generation unit 1750) where appropriate.

The first camera 1700 is operable to capture images of a user within an environment. As noted above, such a camera should be suitable for capturing images that enable the locating of a user within the environment; this camera corresponds in function to the camera 1220 described above, and may be configured in any suitable manner to achieve such function.

The second camera 1710, having a smaller field of view than the first camera, is operable to capture images of at least one of the user's eyes. This camera corresponds in function to the camera 1230 described above, and may be configured in any suitable manner to achieve such function.

As noted above, a reduced field of view may be achieved with an appropriate selection of optics and sensors, for example. The field of view should be selected so as to broadly correspond to angular size of a user's eye or eyes; this may be for a particular reference distance (with a threshold increase in size relative to the eye/eyes to ensure functioning at a closer distance), or may be able to be adjusted during use, for example. Of course, any suitable selection of a field of view for the second camera 1710 may be provided, so long as it is smaller than that of the first camera 1700.

In some examples, the second camera is operable to capture separate images of each of the user's eyes. This may be achieved by implementing the second camera as a pair of cameras or imaging elements, for example, or by using an optical arrangement (such as one or more mirrors) to enable images to be captured of two or more images with discontinuities between them.

In some embodiments, the first and second cameras 1700 and 1710 are formed as a single unit; this is discussed above with reference to the unit 1230 of FIG. 12, for example. Alternatively, it is considered that other arrangements are possible. For instance, the second camera 1710 may held by the user or affixed to a handheld object that is held by a user (such as a game controller). Another exemplary embodiment is that in which the second camera 1710 (and/or the first camera 1700) are formed as a part of (or affixed to) an independent object such as a drone, and that this object may be moved freely within the environment.

As has been noted above, in some embodiments the configurations of the cameras may be modified or selected as appropriate. For example, one or both of the cameras may be operable to capture images using infra-red light (and may comprise an infra-red light source in aid of this). Similarly, one or both of the cameras may comprise a stereoscopic imaging arrangement. In some embodiments, the second camera 1710 comprises one or more sensors (such as accelerometers or gyroscopes) for detecting motion of the camera 1710; where suitable, such sensors may also be provided for the first camera 1700.

The eye identification unit 1720 is operable to identify a location of at least one of the user's eyes from images captured by the first camera 1700. This may be performed using any suitable image processing techniques, and may be assisted by the presence of visual markers or indicators within the captured images as appropriate.

The camera control unit 1730 is operable to modify the position and/or orientation of the second camera in dependence upon the detected location of the at least one of the user's eyes, so as to cause the second camera to be able to capture images of at least one of the user's eyes. In some embodiments, the camera control unit 1730 is operable to cause the second camera to move about the environment, instead of or in addition to any other position/orientation modification.

An example of such control may be in an embodiment in which one or both the cameras 1700 and 1710 comprise a micro-electromechanical system (MEMS) controllable by the camera control unit 1730 so as to allow modification of the position and/or orientation of the camera. The camera control unit 1730 may be operable to determine an appropriate modification to be made, and to generate control signals appropriate to cause a corresponding operation of the MEMS.

In some embodiments, one or both of the cameras 1700 and 1710 comprises a mirror element, and the camera control unit 1730 may be operable to modify the position and/or orientation of the mirror element to cause the corresponding camera to image a different part of the environment. This may be in addition to, or instead of, the modification to position and/or orientation as described above. In some scenarios, it may be advantageous to utilise one or more mirrors to implement a mirror flutter technique for increasing the resolution of images used for processing. Such techniques capture sequential images that are spatially offset from one another by a predetermined amount by modifying the orientation of a mirror at a high frequency; these images may be combined to generate a high-resolution image at half the frame rate of the camera (in the case that two sequential images are used to generate a single image).

It may be considered advantageous that the camera control unit is operable to control camera motion (including either of both of the cameras 1700 and 1710) in dependence upon a predicted movement of the user. This prediction may be generated by any suitable processing unit, and may be based upon assessment of the user's motion, information about an application or process that a user is interacting with, or any other suitable input information.

The gaze direction identification unit 1740 is operable to identify a gaze direction of the user from images captured by the second camera. This may be performed using any suitable image processing method, as has been described above.

The input generation unit 1750 is operable to generate one or more inputs in dependence upon the detected gaze direction. This may include any suitable control of processing, or interaction with an application or game, as appropriate.

The arrangement of FIG. 17 is an example of a processor (for example, a GPU and/or CPU located in a games console or any other computing device) that is operable to perform a gaze tracking method using a first and second camera, the second camera having a smaller field of view than the first camera, and in particular is operable to:

capture images of a user within an environment with the first camera;

identify a location of at least one of the user's eyes from images captured by the first camera;

modify the position and/or orientation of the second camera in dependence upon the detected location of the at least one of the user's eyes, so as to cause the second camera to be able to capture images of at least one of the user's eyes; and identify a gaze direction of the user from images captured by the second camera.

Figure 18:
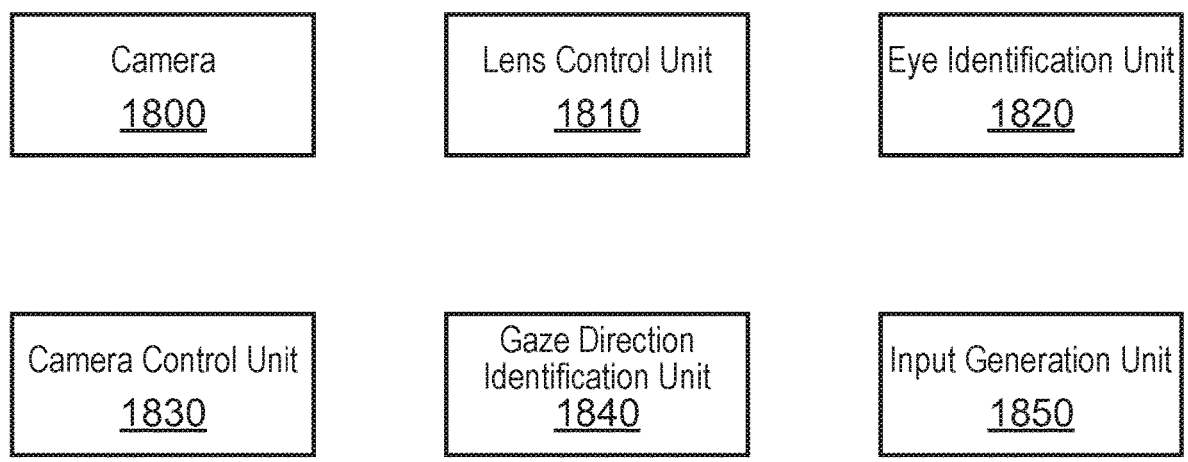
FIG. 18 schematically illustrates a gaze tracking system suitable for implementing embodiments in which a single camera is provided with multiple lenses.

FIG. 18 schematically illustrates a gaze tracking system operable to implement embodiments in which a single camera is provided with multiple lenses to select from so as to alter the field of view of the camera. This system comprises a camera 1800, a lens control unit 1810, an eye identification unit 1820, a camera control unit 1830, a gaze direction identification unit 1840, and an input generation unit 1850. The order and/or location of each of these devices may be selected freely; for example, they may be all formed in a single unit or distributed in any suitable arrangement.

Equally, other hardware elements may be present, and some may be omitted (such as the input generation unit 1850) where appropriate.

Similar units between FIGS. 17 and 18 have been numbered accordingly, and function in largely the same way. Discussion of these elements is therefore limited for the sake of conciseness.

The camera 1800, as described above with reference to FIG. 16, comprises two or more lenses that may be switched between so as to vary the field of view of the camera 1800. This switching is controlled by the lens control unit 1810, which is operable to perform control as appropriate so as to cause a physical switching of the lenses. This switching may be performed in response to a positive detection of the user's eye or eyes in an image (narrowing the field of view), or a loss of a view of the user's eye or eyes (widening the field of view).

The arrangement of FIG. 18 is an example of a processor (for example, a GPU and/or CPU located in a games console or any other computing device) that is operable to perform gaze tracking using a camera with multiple lenses to alter the field of view of the camera, and in particular is operable to:

- capture images of a user within an environment using the camera with a wide field of view lens;
- identify the location at least one of the user's eyes from images captured by the camera;
- switch lenses so as to narrow the field of view, and optionally modifying the position and/or orientation of the camera in dependence upon the location of the user's eye or eyes;
- identify a gaze direction of the user from images captured by the camera using a narrower field of view lens.

FIG. 19 schematically illustrates a gaze tracking method suitable for implementing a number of the embodiments described above.

A step 1900 comprises capturing images of a user within an environment with the first camera.

A step 1910 comprises identifying a location of at least one of the user's eyes from images captured by the first camera.

A step 1920 comprises modifying the position and/or orientation of the second camera in dependence upon the detected location of the at least one of the user's eyes, so as to cause the second camera to be able to capture images of at least one of the user's eyes.

A step 1930 comprises identifying a gaze direction of the user from images captured by the second camera.

An optional step 1940 comprises generating one or more inputs in dependence upon the detected gaze direction.

FIG. 20 schematically illustrates a gaze tracking method suitable for implementing embodiments in which a single camera is provided with multiple lenses to select from so as to alter the field of view of the camera.

A step 2000 comprises capturing images of a user within an environment using the camera with a wide field of view lens.

A step 2010 comprises identifying the location at least one of the user's eyes from images captured by the camera.

A step 2020 comprises switching lenses so as to narrow the field of view, and optionally modifying the position and/or orientation of the camera in dependence upon the location of the user's eye or eyes.

A step 2030 comprises identifying a gaze direction of the user from images captured by the camera using a narrower field of view lens.

An optional step 2040 comprises generating one or more inputs in dependence upon the detected gaze direction.

The techniques described above may be implemented in hardware, software or combinations of the two. In the case that a software-controlled data processing apparatus is employed to implement one or more features of the embodiments, it will be appreciated that such software, and a storage or transmission medium such as a non-transitory machine-readable storage medium by which such software is provided, are also considered as embodiments of the disclosure.

Thus, the foregoing discussion discloses and describes merely exemplary embodiments of the present invention. As will be understood by those skilled in the art, the present invention may be embodied in other specific forms without departing from the spirit or essential characteristics thereof. Accordingly, the disclosure of the present invention is intended to be illustrative, but not limiting of the scope of the invention, as well as other claims. The disclosure, including any readily discernible variants of the teachings herein, defines, in part, the scope of the foregoing claim terminology such that no inventive subject matter is dedicated to the public.

Embodiments of the present disclosure may be implemented in accordance with any one or more of the following numbered clauses:

1. A gaze tracking system comprising:
   - a first camera operable to capture images of a user within an environment;
   - a second camera, having a smaller field of view than the first camera, operable to capture images of at least one of the user's eyes;
   - an eye identification unit operable to identify a location of at least one of the user's eyes from images captured by the first camera;
   - a camera control unit operable to modify the position and/or orientation of the second camera in dependence upon the detected location of the at least one of the user's eyes, so as to cause the second camera to be able to capture images of at least one of the user's eyes; and
   - a gaze direction identification unit operable to identify a gaze direction of the user from images captured by the second camera.

2. A system according to clause 1, wherein the first and second cameras are formed as a single unit.

3. A system according to clause 1, wherein the second camera is held by the user or affixed to a handheld object.

4. A system according to clause 1, wherein the camera control unit is operable to cause the second camera to move about the environment.

5. A system according to any preceding clause, wherein one or both of the cameras is operable to capture images using infra-red light.

6. A system according to any preceding clause, wherein the second camera is operable to capture separate images of each of the user's eyes.

7. A system according to any preceding clause, wherein one or both of the cameras comprise a stereoscopic imaging arrangement.

8. A system according to any preceding clause, wherein the second camera comprises one or more sensors for detecting motion of the camera.

9. A system according to any preceding clause, wherein:
   - one or both of the cameras comprises a mirror element, and
   - the camera control unit is operable to modify the position and/or orientation of the mirror element to cause the corresponding camera to image a different part of the environment.

10. A system according to any preceding clause, wherein one or both the cameras comprise a micro-electromechanical system controllable by the camera control unit so as to allow modification of the position and/or orientation of the camera.

11. A system according to any preceding clause, wherein the camera control unit is operable to control camera motion in dependence upon a predicted movement of the user.

12. A system according to any preceding clause, comprising an input generation unit operable to generate one or more inputs in dependence upon the detected gaze direction.

13. A gaze tracking method for performing tracking using a first camera and a second camera, the second camera having a smaller field of view than the first camera, the method comprising:

capturing images of a user within an environment with the first camera;

identifying a location of at least one of the user's eyes from images captured by the first camera;

modifying the position and/or orientation of the second camera in dependence upon the detected location of the at least one of the user's eyes, so as to cause the second camera to be able to capture images of at least one of the user's eyes; and identifying a gaze direction of the user from images captured by the second camera.

14. Computer software which, when executed by a computer, causes the computer to carry out the method of clause 13.

15. A non-transitory machine-readable storage medium which stores computer software according to clause 14.

The invention claimed is:

1. A gaze tracking system comprising:
a first camera operable to capture images of a user within an environment, where the first camera is neither held by the user nor affixed to a handheld object to be held by the user;
a second camera, having a smaller field of view than the first camera, operable to capture images of at least one of the user's eyes, where the second camera is at least one of held by the user or affixed to a handheld object to be held by the user;
an eye identification unit operable to identify a location of at least one of the user's eyes from images captured by the first camera;
a camera control unit operable to modify the position and/or orientation of the second camera in dependence upon the detected location of the at least one of the user's eyes, so as to cause the second camera to be able to capture images of at least one of the user's eyes; and
a gaze direction identification unit operable to identify a gaze direction of the user from images captured by the second camera.

2. The system of claim 1, wherein the camera control unit is operable to cause the second camera to move about the environment.

3. The system of claim 1, wherein one or both of the cameras is operable to capture images using infra-red light.

4. The system of claim 1, wherein the second camera is operable to capture separate images of each of the user's eyes.

5. The system of claim 1, wherein one or both of the cameras comprise a stereoscopic imaging arrangement.

6. The system of claim 1, wherein the second camera comprises one or more sensors for detecting motion of the camera.

7. The system of claim 1, wherein:
one or both of the cameras comprises a mirror element, and
the camera control unit is operable to modify the position and/or orientation of the mirror element to cause the corresponding camera to image a different part of the environment.

8. The system of claim 1, wherein one or both the cameras comprise a micro-electromechanical system controllable by the camera control unit so as to allow modification of the position and/or orientation of the camera.

9. The system of claim 1, wherein the camera control unit is operable to control camera motion in dependence upon a predicted movement of the user.

10. The system of claim 1, comprising an input generation unit operable to generate one or more inputs in dependence upon the detected gaze direction.

11. A gaze tracking method for performing tracking using a first camera operable to capture images of a user within an environment and which is neither held by the user nor affixed to a handheld object to be held by the user, and a second camera having a smaller field of view than the first camera, being operable to capture images of at least one of the user's eyes, and which is at least one of held by the user or affixed to a handheld object to be held by the user, the method comprising:
capturing images of a user within an environment with the first camera;
identifying a location of at least one of the user's eyes from images captured by the first camera;
modifying the position and/or orientation of the second camera in dependence upon the detected location of the at least one of the user's eyes, so as to cause the second camera to be able to capture images of at least one of the user's eyes; and
identifying a gaze direction of the user from images captured by the second camera.

12. A non-transitory machine-readable storage medium which stores computer software which, when executed by a computer, causes the computer to perform a method for performing tracking using a first camera operable to capture images of a user within an environment and which is neither held by the user nor affixed to a handheld object to be held by the user, and a second camera having a smaller field of view than the first camera, being operable to capture images of at least one of the user's eyes, and which is at least one of held by the user or affixed to a handheld object to be held by the user, the method comprising:
capturing images of a user within an environment with the first camera;
identifying a location of at least one of the user's eyes from images captured by the first camera;
modifying the position and/or orientation of the second camera in dependence upon the detected location of the at least one of the user's eyes, so as to cause the second camera to be able to capture images of at least one of the user's eyes; and
identifying a gaze direction of the user from images captured by the second camera.

* * * * *